(12) United States Patent
Fritz

(10) Patent No.: US 7,283,223 B2
(45) Date of Patent: Oct. 16, 2007

(54) CYTOMETER HAVING TELECENTRIC OPTICS

(75) Inventor: Bernard S. Fritz, Eagan, MN (US)

(73) Assignee: Honeywell International Inc., Morristown, NJ (US)

( * ) Notice: Subject to any disclaimer, the term of this patent is extended or adjusted under 35 U.S.C. 154(b) by 376 days.

(21) Appl. No.: 10/953,197

(22) Filed: Sep. 28, 2004

(65) Prior Publication Data

US 2006/0066840 A1   Mar. 30, 2006

Related U.S. Application Data

(63) Continuation-in-part of application No. 10/225,325, filed on Aug. 21, 2002, now Pat. No. 6,970,245, and a continuation-in-part of application No. 10/304,773, filed on Nov. 26, 2002.

(51) Int. Cl.
*G01J 1/42* (2006.01)
*G01J 3/30* (2006.01)
*G01N 21/00* (2006.01)

(52) U.S. Cl. ................... 356/218; 356/73; 356/318

(58) Field of Classification Search ............... 356/218, 356/72, 410, 436–444, 201.1, 250; 250/205, 250/573
See application file for complete search history.

(56) References Cited

U.S. PATENT DOCUMENTS 3,822,095 A   7/1974   Hirschfeld
3,976,862 A   8/1976   Curbelo
4,478,076 A   10/1984  Bohrer
4,478,077 A   10/1984  Boher
4,501,144 A   2/1985   Higashi et al.
4,651,564 A   3/1987   Johnson et al.

(Continued)

FOREIGN PATENT DOCUMENTS

EP   1001326   5/1999

(Continued)

OTHER PUBLICATIONS

Klaus Henkel, "Die Mikrofibel" 'Online' Jun. 14, 2003, pp. 65-68, Retrieved from the Internet on Jan. 19, 2006, URL:http://www.mikroskopie-muenchen.de/mikrofibel.pdf.

(Continued)

*Primary Examiner*—Layla G. Lauchman
*Assistant Examiner*—J Underwood
(74) *Attorney, Agent, or Firm*—Kris T. Fredrick

(57) ABSTRACT

A mechanism for moving and positioning a light source so that its light impinges a target as it moves on or off axis of an optical system. A detector may receive scattered light at a same position whether the light impinging the target is on or off axis due to, for example, a telecentric optical system. Further, the light may be positioned so that the detector is maximally impinged with scattered light. An output may go to a processor that sends a signal to the light source to move the emitted light so as to continually impinge the target as it moves on or off axis. An array of light sources may used in lieu of the moving light source. To move the light beam, another light at another position in the array may be selected to replace a previously selected light source.

37 Claims, 3 Drawing Sheets

U.S. PATENT DOCUMENTS

| | | |
|---|---|---|
| 4,683,159 A | 7/1987 | Bohrer et al. |
| 4,695,034 A | 9/1987 | Shimizu et al. |
| 4,745,279 A | 5/1988 | Karkar et al. |
| 4,852,985 A | 8/1989 | Fujihara et al. |
| 4,874,949 A | 10/1989 | Harris et al. |
| 4,911,616 A | 3/1990 | Laumann, Jr. |
| 5,050,429 A | 9/1991 | Nishimoto et al. |
| 5,078,581 A | 1/1992 | Blum et al. |
| 5,082,242 A | 1/1992 | Bonne et al. |
| 5,085,562 A | 2/1992 | van Lintel |
| 5,096,388 A | 3/1992 | Weinberg |
| 5,108,623 A | 4/1992 | Cangelosi et al. |
| 5,125,737 A | 6/1992 | Rodriquez et al. |
| 5,129,794 A | 7/1992 | Beatty |
| 5,171,132 A | 12/1992 | Miyazaki et al. |
| 5,176,358 A | 1/1993 | Bonne et al. |
| 5,185,641 A | 2/1993 | Igushi et al. |
| 5,194,909 A | 3/1993 | Tycko |
| 5,219,278 A | 6/1993 | van Lintel |
| 5,224,843 A | 7/1993 | van Lintel |
| 5,244,537 A | 9/1993 | Ohnstein |
| 5,323,999 A | 6/1994 | Bonne et al. |
| 5,441,597 A | 8/1995 | Bonne et al. |
| 5,452,878 A | 9/1995 | Gravesen et al. |
| 5,528,045 A | 6/1996 | Hoffman et al. |
| 5,570,193 A | 10/1996 | Landa et al. |
| 5,601,080 A | 2/1997 | Oppenheimer |
| 5,616,501 A | 4/1997 | Rodriguez |
| 5,631,730 A | 5/1997 | Chupp et al. |
| 5,633,724 A | 5/1997 | King et al. |
| 5,683,159 A | 11/1997 | Johnson |
| 5,691,486 A | 11/1997 | Behringer et al. |
| 5,716,852 A | 2/1998 | Yager et al. |
| 5,726,751 A | 3/1998 | Altendorf et al. |
| 5,757,476 A | 5/1998 | Nakamoto et al. |
| 5,760,900 A * | 6/1998 | Ito et al. ..................... 356/338 |
| 5,793,485 A * | 8/1998 | Gourley ...................... 356/318 |
| 5,799,030 A | 8/1998 | Brenner |
| 5,822,170 A | 10/1998 | Cabuz et al. |
| 5,836,750 A | 11/1998 | Cabuz |
| 5,863,502 A | 1/1999 | Southgate et al. |
| 5,880,474 A | 3/1999 | Norton et al. |
| 5,893,722 A | 4/1999 | Hibbs-Brenner et al. |
| 5,901,939 A | 5/1999 | Cabuz et al. |
| 5,922,210 A | 7/1999 | Brody et al. |
| 5,932,100 A | 8/1999 | Yager et al. |
| 5,948,684 A | 9/1999 | Weigl et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,032,689 A | 3/2000 | Tsai et al. |
| 6,082,185 A | 7/2000 | Saaski |
| 6,097,485 A | 8/2000 | Lievan |
| 6,106,245 A | 8/2000 | Cabuz |
| 6,109,889 A | 8/2000 | Zengerie et al. |
| 6,139,800 A | 10/2000 | Chandler |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,237,619 B1 | 5/2001 | Maillefer et al. |
| 6,240,944 B1 | 6/2001 | Ohnstein et al. |
| 6,249,341 B1 | 6/2001 | Basiji et al. |
| 6,281,975 B1 | 8/2001 | Munk |
| 6,382,228 B1 | 5/2002 | Cabuz et al. |
| 6,549,275 B1 | 4/2003 | Cabuz et al. |
| 6,862,090 B2 * | 3/2005 | Chen et al. .................. 356/300 |
| 2002/0067550 A1 | 6/2002 | Mizouchi |
| 2003/0058445 A1 | 3/2003 | Fritz et al. |

FOREIGN PATENT DOCUMENTS

| | | |
|---|---|---|
| EP | 1258743 | 11/2002 |
| WO | WO95/27199 | 3/1995 |
| WO | WO99/60397 | 4/1999 |
| WO | WO01/09598 | 7/2000 |

OTHER PUBLICATIONS http://www.micronics.net/tensor.htm, pp. 1-4, downloaded Jun. 14, 2000.

http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Differential Blood Cell Counts Obtained Using A Microchannel Based Flow Cytometer", Solid State Sensors & Actuators, vol. 1, 531, 1997.

Altendorf et al., "Microfabrication Technology For Research And Diagnostics, Silicon Microchannel Optical Flow Cytometry", SPIE Proceedings, Biomedical Optics 96, Jan. 1996.

Altendorf et al., "Results Obtained Using A Prototype Microfluidics-Based Hematology Analyzer", SPIE Biomedical Optics 97, 1997.

Cabuz, et al., "Mesoscopic Sampler Based on 3D Array of Electrostatically Activated Diaphragms", Transducers '99, The 10th International Conference on Solid-State Sensors and Actuators, Digest of Technical Papers, vol. 2, Jun. 7-10, 1999.

Darling et al., "Integration Of Microelectrodes With Etched Microchannels For In-Stream Electrochemical Analysis", MicroTAS 98, Banff, Canada, Apr. 1998.

Hatch et al., "Microfluidic Approaches To Immunoassays", SPIE conference on Micromachining and Microfabrication Symposium at Santa Clara, CA, Sep. 20-22, 1999.

Huang. et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb; 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10, No. 4. pp. 482-491, Dec. 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen, et al., "Four-Parameter White Blood Cell Differential Counting Based on Light Scattering Measurements", Alan R. Liss, Inc., Cytometry 9:39-43, 1988.

Weigl et al., "Silicon-microfabricated diffusion-based optical chemical sensor," Sensors and Actuators, B 38-39, pp. 452-457, 1997.

Weigl et al., "Diffusion-Based Optical Chemical Detection In Silicon Flow Structures", Analytical Methods & Instrumentation, µTTAS 96 special edition, 1996.

Weigl et al., "Microfluidic Diffusion-Based Separation And Detection", Science, vol. 283, pp. 346-347, Jan. 15, 1999.

Weigl et al., "Optical And Electrochemical Diffusion-Based Detection Of Analytes In Complex Samples Using Microfabricated Flow Structures (T-SensorSTM)", Micro- and nanofabn'cated electrooptical mechanical systems for biomedical and environmental applications II- SPIE vol. 3606, Jan. 25-26, 1999.

Weigl et al., "Rapid Sequential Chemical Analysis Using Multiple Fluorescent Reporter Beads", μTTAS 96 Conference Proceedings, 1996.

Weigl et al., "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Weigl, et al., "Fluorescence and Absorbance Analyte Sensing In Whole Blood Based On Diffusion Separation In Silicon-Microfabricated Flow Structures," SPIE Proceedings, J. Lakowitz (ed.), Advances in Fluorescence Sensing Technology III, pp. 171-181.

Yager et al., "Design Of Microfluidic Sample Preconditioning Systems For Detection Of Biological Agents In Environmental Samples", SPIE Proceedings, 3515, 252-259, 1998.

Yager et al., "Applying Microfluidic Chemical Analytical Systems To Imperfect Samples", Micro Total Analysis Systems 98, Kluwer Academic Publishers, Dordrecht, 207-212, 1998.

* cited by examiner

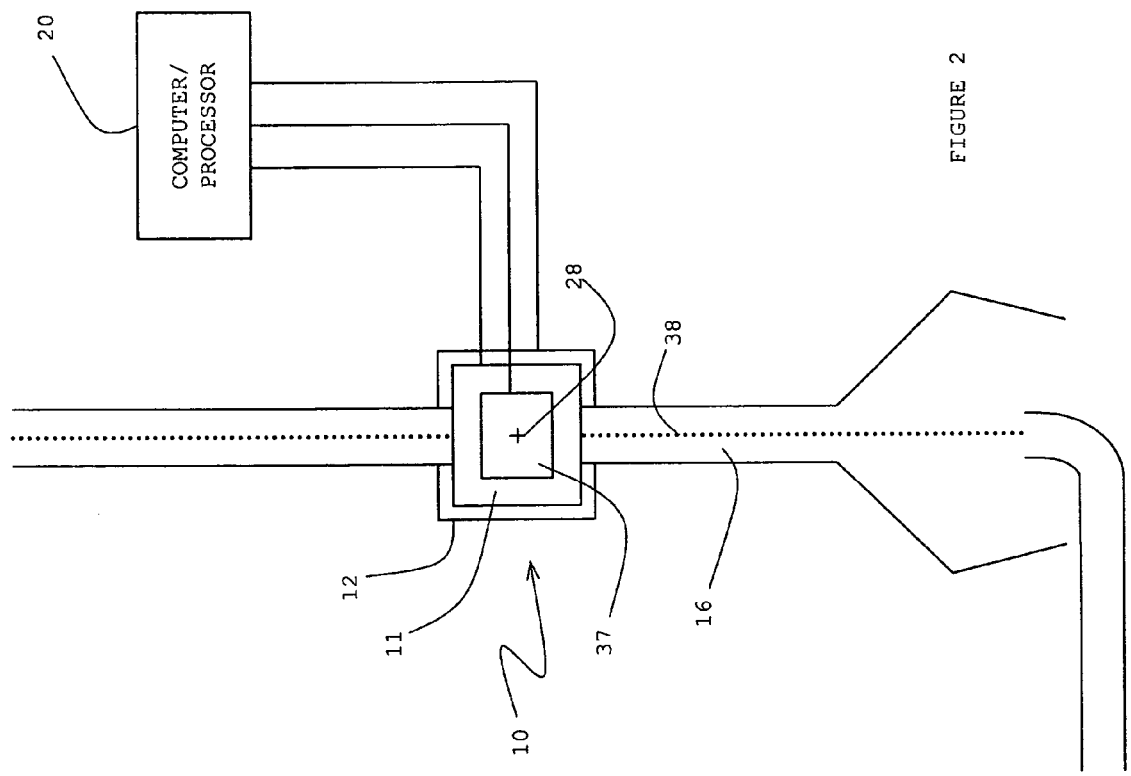

ns to be
CYTOMETER HAVING TELECENTRIC OPTICS

The present application claims the benefit under 35 USC § 120 as a continuation-in-part of U.S. patent application Ser. No. 10/225,325, filed Aug. 21, 2002, now U.S. Pat. No. 6,970,245, issued Nov. 29, 2005, and as a continuation-in-part of pending U.S. patent application Ser. No. 10/304,773, filed Nov. 26, 2002.

BACKGROUND

The present invention relates generally to flow cytometers. More particularly, the present invention relates to flow cytometers that sense optical properties of microscopic particles or components in a flow stream with light.

This invention is related to U.S. patent application Ser. No. 10/225,325, by Bernard Fritz et al., filed Aug. 21, 2002, and entitled "Optical Alignment Detection System", which is incorporated herein by reference; and the invention is related to U.S. patent application Ser. No. 10/304,773, by Aravind Padmanabhan et al., filed Nov. 26, 2002, and entitled "Portable Scattering and Fluorescence Cytometer", which is incorporated herein by reference. This invention also is related to U.S. Pat. No. 6,549,275 B1, by Cabuz et al., issued Apr. 15, 2003, and entitled "Optical Detection System for Flow Cytometry"; U.S. Pat. No. 6,597,438 B1, by Cabuz et al., issued Jul. 22, 2003, and entitled "Portable Flow Cytometer"; U.S. Pat. No. 6,382,228 B1, by Cabuz et al., issued May 7, 2002, and entitled "Fluid Driving System for Flow Cytometry"; U.S. Pat. No. 6,700,130 B2, issued Mar. 2, 2004, by Fritz, and entitled "Optical Detection System for Flow Cytometry"; and U.S. Pat. No. 6,240,944 B1, by Ohnstein et al., issued Jun. 5, 2001, and entitled "Addressable Valve Arrays for Proportional Pressure or Flow Control"; all of which are incorporated herein by reference. The above-noted applications and patents are owned by the same entity. The term "fluid" may be used here as a generic term that includes gases and liquids as species.

SUMMARY

The invention may be a mechanism for moving and positioning a light source so that its light impinges a target as it moves on or off axis of an optical system. A detector may receive scattered light at a same position whether the light impinging the target is on or off axis due to, as an illustrative example, a telecentric optical system. Further, the light may be positioned so that the detector is maximally impinged with scattered light. An output may go to a processor that sends a signal to the light source to move the emitted light so as to continually impinge the target as it moves on or off axis. An array of light sources may used in lieu of the moving light source. To move the light beam, another light at another position in the array may be selected to replace a previously selected light source.

BRIEF DESCRIPTION OF THE DRAWINGS

FIG. 2 shows another view of the beam adjuster along with a computer in conjunction with the channel to be illuminated by the beam.

DESCRIPTION

Figure 1A:
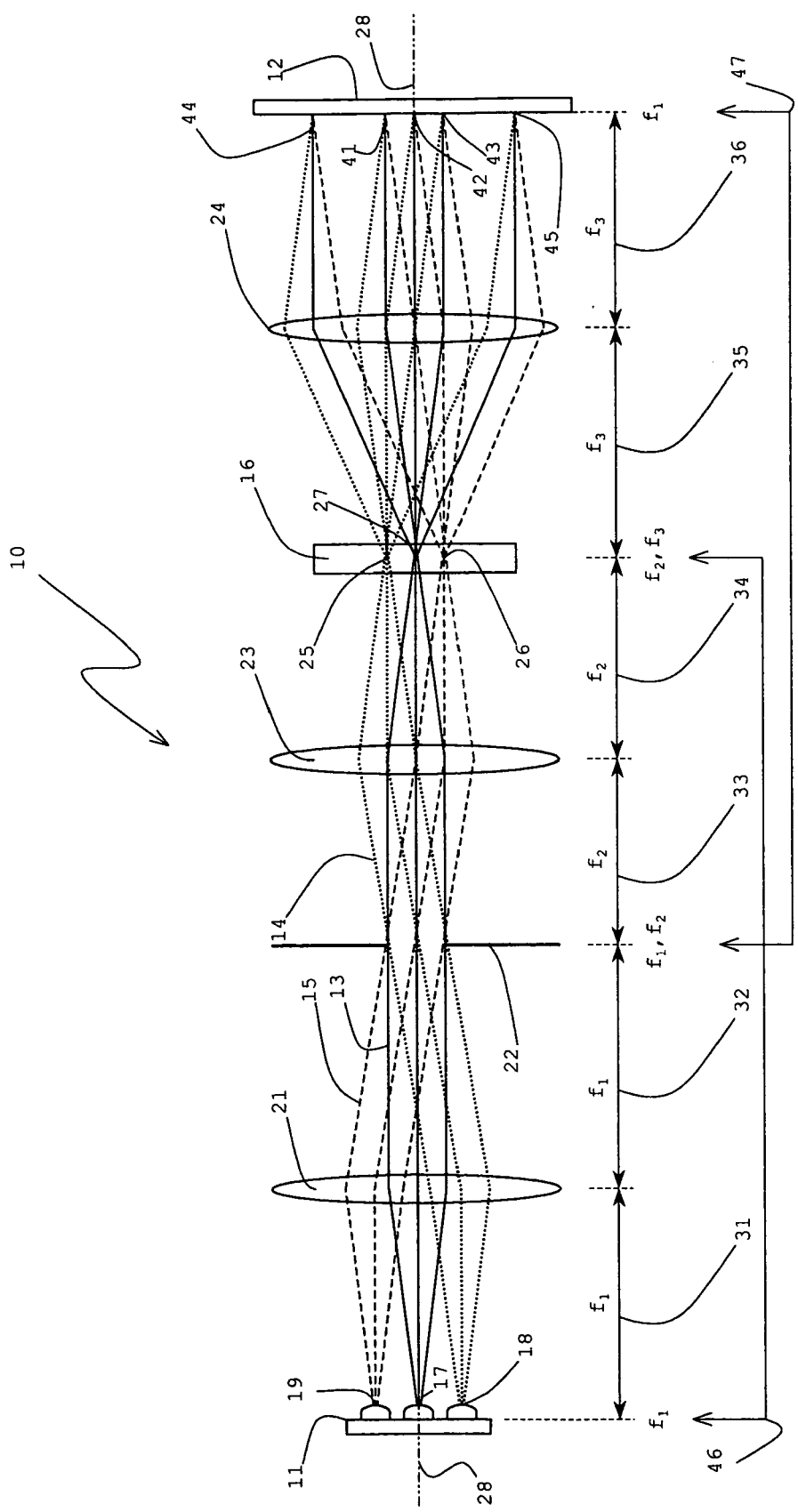
FIGS. 1a and 1b are diagrams of a beam position adjuster along with associated optics for a channel of a cytometer or similar mechanism.

FIG. 1a is a schematic of a device that may provide for the use of an optical telecentricity condition in an optical layout of a flow cytometer. The condition may allow the use of off-axis field points for a light source 11 such that the illumination conditions at the flow channel are similar to that of an on-axis source. The same may be true for the detector or detectors 12 collecting the scattered light from the flow channel. This condition may allow the use of an array or moving source to illuminate the flow channel and maintain similar optical conditions at the detector as those for the on-axis source position. By allowing the source to move, it allows one to track the position of the flow activity, especially particles in the flow stream of a cytometer, and yet keep the same position of the light impinging the detector 12.

The telecentric condition is where the aperture stop 22 of an optical system 10 is located at the focal point or focus of the lens 21 and the focal point of lens 23. Having the optical system meet this condition on both the source 11 side and the detector 12 side of the flow cytometer allows equivalence of the optical system for off-axis field points.

The optical system 10 of FIG. 1a is shown as a setup for the telecentric condition for both the source 11 and detector 12 legs. The case for the source 11 on axis is the solid line optical path 13. The dotted line 14 and dashed line 15 optical paths may indicate source 11 off-axis light beams. In going from the on-axis to an off-axis source 11, the focused spot at the flow channel 16 is displaced laterally but the cone angle and orientation remain the same as for the on-axis case. At the detector array 12, the same scattering angle, solid, dotted or dashed line paths 13, 14 or 15, respectively, of the light of any position of the source 11, may be mapped to the same positions 41, 42, and 43 on the detector array 12.

Illumination along the solid line paths 13 may emanate on axis from a source 17 of array 11 and proceed through a collimating lens 21. Source 17 illumination may proceed through an aperture stop 22 onto a lens 23. A source 17 light beam may be focused on flow channel 16 and detector 12, along solid-line paths 13. Scattered light due to the beam along paths 13 may proceed through a lens 24 to be focused on detector array 12 at places 44 and 45 of detector 12.

If a core stream in the cytometer channel 16 is shifted off axis to a position 25 of channel 16, the illumination may be shifted to off-axis dotted-line paths 14. Light from a source 18 may proceed along the light paths 14 through lens 21, aperture 22 and lens 23 to channel 16. Illumination from paths 14 may be scattered in channel 16 and focused on detector array 12 at positions 44 and 45 of detector 12.

If the core stream 38 in the cytometer channel 16 is at a position 26 of the channel, the focus of illumination may be shifted to position 26 of the channel. Illumination from a source 19 of array 11 may proceed along dashed-line paths 15 through lens 21, aperture 22 and lens 23 to position 26 of channel 16. Scattered light from position 26 may proceed along paths 15 through lens 24 to be focused on detector array 12 at positions 44 and 45.

The optical elements of system 10 are coincident focal lengths apart. For instance, lens 21 is a focal length ($f_1$) 31 from the light source or array 11 and focal length ($f_1$) 32 from aperture stop 22. The lengths 31 and 32 may each be the focal length ($f_1$) of lens 21. Lengths 33 and 34 of lens 23 from the aperture stop 22 and channel 16, respectively, may each be the focal length ($f_2$) of lens 23. Lengths 35 and 36 of lens 24 from channel 16 may each be the focal length ($f_3$) of lens 24. Line 46 indicates the conjugate planes 11 and 16 at the light source and the channel. Line 47 indicates the conjugate planes 22 and 12 at the aperture and detector, respectively.

Light array 11 may have light sources 17, 18 and 19 which are turned on one at a time according to the location of the core stream in channel 16. There may be more light sources in the array for a more refined adjustment of the location of the light beam impinging the channel 16. Array 11 may be two-dimensional.

Instead, detector array 11 may have one source, e.g., source 17, which moves across the array structure in an x and/or y direction to provide an adjustment of the location of the light impinging the channel 16. The light source may be incremented with a stepper motor like mechanism 37 laterally across the array to move the location of impinging light in channel 16 laterally.

Light beams along paths 13, 14 and 15 may be scattered by particles in channel 16 to portions 44 and 45 of detector 12. Detector 12 may convert the light detected at portions 44 and 45, and positions 41, 42 and 43, into electrical signals which may be sent to a processor 10 which may process the electrical signals into information about the particles of flow stream 38 in the channel 16.

Figure 1B:
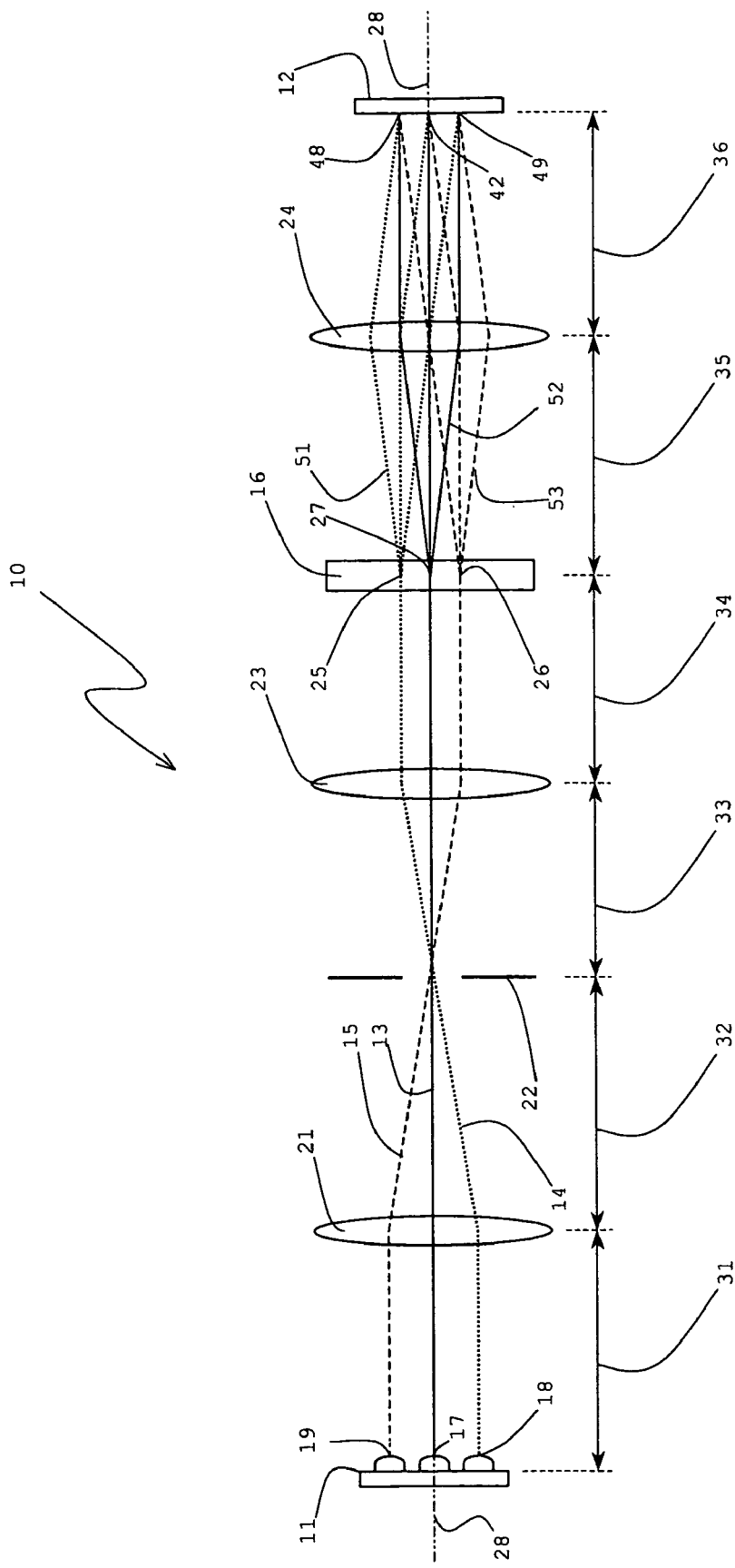

FIG. 1b shows the light, without the light cones, from the light sources 17, 18 and 19 along paths 13, 14 and 15, respectively. The light beams may be scattered by particles in channel 16 as shown by cones 51, 52 and 53. Scattered light may impinge locations 48 and 49 on detector 12.

FIG. 2 is a diagram showing the optical system 10 with a computer/processor 20 for control of the light source 11. One version of control is to select from an array 11 of light sources to determine the position of the impingement of light in the channel 16 of a cytometer. The other version is having a light source that is moved to provide impingement of the light beam in alignment with the core stream 38 even though the core stream may be off the axis 28 (which may be perpendicular to the surface of the paper of FIG. 2) of the optical system 10 and channel 16. A stepper motor 37 may move the light sources, say, source 17, from side-to-side to stay aligned with the core stream 38.

When the light sensor is aligned with the core stream 38, the light beam impinging particles in the core stream 38 may be scattered by the particles. Detector 12 may be a scattered light detector and a direct light detector, such as a linear array or an annular-shaped detector array. Detector 12 may have independent detector portions for various angles of scattered light and for non-scattered light. The annular array may provide a 360 range of detection by the various portions for the telecentricity system. Detector 12 may provide an electrical signal representative of the scattered light impinging the detector. If the light beam from the light source of assembly 11 is not impinging particles of the core stream 38, then there may be little scattered light detected by detector 12 with little electrical signal from this detector but rather non-scattered light. Detector 12 may detect forward-angle light scatter (FALS), small-angle light scatter (SALS), and large-angle light scatter (LALS).

The electrical signal from detector 12 may go to a computer/processor 20. The computer/processor 20 may send a signal to light source array 11 to indicate the selection of another light source or the movement of a single light source to shift the position of where the light beam is impinging in the channel 11. The position may be located and the light beam moved so that there is a maximum signal at the output of detector 12. That may mean that the light beam is creating a maximum scattering signal at detector 12. The computer 20 may send a signal that changes the position or location of the light beam in channel 16 by selecting a different light source of array 11 or moving a light source to seek out a maximum scattering signal from detector 12 to computer 20. Effectively, there is a feedback loop consisting of computer 20 to light source 11, light beam from the source scattering in the channel 16, a detector 12 providing the electrical representation of the scattered light to the computer. The computer 20 may send a signal to light source 11 to maximize the scattering signal which tends to keep the light beam focused on the core stream 38, whether on-axis or not.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. An illumination apparatus comprising:
   a light source;
   an optical system, having an axis, at least partially situated between the light source and a target; and
   a detector situated on the axis and proximate to the target; and
   wherein:
   the target moves on axis or off axis;
   the light source provides a light beam that is moveable to illuminate the target on axis or off axis;
   light from the light beam is mapped to a first position on the detector when the light source is on axis;
   light from the light beam is mapped to a second position on the detector when the light source is off axis;
   the second position is equivalent to the first position;
   the illumination apparatus further comprises: a mechanism connected to the light source to provide various positions of the light source that moves the light beam; and
   a processor connected to the detector and the mechanism.

2. The apparatus of claim 1, wherein the optical system comprises:
   a first lens between the light source and the target; and
   an aperture situated between the first lens and the target.

3. The apparatus of claim 2, wherein the optical system further comprises a second lens situated between the aperture and the target.

4. The apparatus of claim 3, wherein the optical system further comprises a third lens situated between the target and the detector.

5. The apparatus of claim 4, wherein:
   the light source is situated substantially at a focal point of the first lens;
   the aperture is situated substantially at a focal point of the first lens and a focal point of the second lens;
   the target is situated substantially at a focal point of the second lens and a focal point of the third lens; and
   the detector is situated substantially at a focal point of the third lens.

6. The apparatus of claim 1, wherein at least some of the light mapped on the first position and the second position of the detector is light scattered by the target.

7. The apparatus of claim 1, wherein a signal from the detector via the processor indicates a position to be selected of the various positions of the light source to maximally impact the detector with light.

8. A telecentric light source position aligner system, comprising:
a light source, moveable for various positions, situated proximate to a channel;
a detector having the channel situated between the detector and the light source; and
a processor connected to the light source and the detector; and
wherein:
the detector converts detected scattered light into an electrical signal;
the electrical signal goes to the processor; and
the processor sends a signal to the light source to adjust a position of the light source to optimize the electrical signal from the detector.

9. The system of claim 8, wherein:
the light source has an optical path from the light source through the channel; and
the light path is from the channel to a specific location on the detector.

10. The system of claim 9, wherein for the various positions of the light source, the light path from the light source at each of the various positions is to the specific location on the detector.

11. The system of claim 8, wherein:
the light source emanates light;
the light impinges the channel; and
some of the light becomes scattered light; and
the detector detects the scattered light.

12. The system of claim 11, wherein:
the amount of scattered light varies with an alignment of the incident light with a core stream within the channel of a cytometer; and
a varying position of the light source varies the alignment of the incident light with the core stream.

13. The system of claim 12, wherein a varying position of the light source does not vary the location of impingement of light on the detector from the light source.

14. A telecentric light source position aligner system, comprising:
a light source, moveable for various positions, situated proximate to a channel;
a detector having the channel situated between the detector and the light source; and
a processor connected to the light source and the detector; and
wherein:
the light source emanates light;
the light impinges the channel;
some of the light becomes scattered light;
the detector detects the scattered light;
the amount of scattered light varies with an alignment of the incident light with a core stream within the channel of a cytometer;
a varying position of the light source varies the alignment of the incident light with the core stream;
the detector converts detected scattered light into an electrical signal;
the electrical signal goes to the processor; and
the processor sends a signal to the light source to adjust a position of the light source to optimize the electrical signal from the detector.

15. The system of claim 14, wherein light on the detector from the light source has a cone angle and orientation that remains the same.

16. A light beam alignment system comprising:
a detector proximate to a channel; and
a light source having an alignment adjuster relative to the channel; and
wherein:
the alignment adjuster provides a projection of the light source on a moveable target in the channel without affecting a projection of the light source relative to the detector;
an amplitude of an electrical signal from the detector indicates an amount of projection of the light source relative to the target;
the greater the amplitude of the electrical signal, the projection of the light source is closer to the target; and
the lesser of the amplitude of the electrical signal, the projection of the light source is farther from the target.

17. The system of claim 16, wherein the alignment adjuster comprises an optical structure for focusing the light source on the moveable target in the channel and at a consistent location on the detector.

18. The system of claim 17, wherein light from the light source to the detector has a cone angle and orientation that remains the same.

19. The system of claim 17, wherein:
the detector is connected to a processor; and
the processor is connected to the alignment adjuster.

20. The system of claim 19, wherein:
light from the light source impinges the target;
the target scatters the light that impinges the target;
the detector converts the scattered light into a first electrical signal; and
the processor measures an amplitude of the first electrical signal and sends a second electrical signal to the alignment adjuster to provide the projection of the light source on a moveable target in the channel.

21. A light beam alignment system comprising:
a detector proximate to a channel; and
a light source having an alignment adjuster relative to the channel; and
wherein:
the alignment adjuster provides a projection of the light source on a moveable target in the channel without affecting a projection of the light source relative to the detector;
the alignment adjuster comprises an optical structure for focusing the light source on the moveable target in the channel and at a consistent location on the detector;
the detector is connected to a processor;
the processor is connected to the alignment adjuster;
light from the light source impinges the target;
the target scatters the light that impinges the target;
the detector converts the scattered light into a first electrical signal;
the processor measures an amplitude of the first electrical signal and sends a second electrical signal to the alignment adjuster to provide the projection of the light source on a moveable target in the channel;
the amplitude of the first electrical signal from the detector indicates an amount of projection of the light source relative to the target;
the greater the amplitude of the first electrical signal, the projection of the light source is closer to the target; and
the lesser of the amplitude of the first electrical signal, the projection of the light source is farther from the target.

22. The system of claim 21, wherein the target is in a core stream in the channel of a cytometer.

23. The system of claim 22, wherein the core stream has a location that may change within the channel.

24. A means for alignment comprising:
means for providing a light beam having a direction;
means for adjusting the direction of the light beam;
means for providing a target;
means for measuring the amount of light scattered by the target; and
wherein the direction of the light beam is adjusted to increase the amount of light scattered by the target.

25. The means of claim 24, wherein:
the light scattered by the target is mapped to a first position of the means for measuring the amount of light scattered by the target; and
upon an adjustment of the direction of the light beam, the light scattered by the target remains mapped to the first position of the means for measuring the amount of light scattered by the target.

26. The means of claim 25, wherein the target is a core stream in a flow channel of a cytometer.

27. A method for alignment of a light beam with a core stream in a flow channel of a cytometer, comprising:
directing a light beam towards the flow channel;
measuring an amount of light scattered by the core stream in the flow channel; and
adjusting the direction of the light beam towards the core stream to change the amount of light scattered by the flow stream; and
wherein the direction of the light beam towards the core stream is adjusted to maximize the amount of light scattered by the flow stream.

28. The method of claim 27, wherein the direction of the light beam is adjusted with a change of position of a light source relative to the core stream.

29. The method of claim 28, wherein light on the core stream from the light source has a cone angle and orientation that remains the same.

30. The method of claim 29, wherein:
the light source comprises a plurality of lights; and
the change of position of the light source is effected by a selection of a light from the plurality of lights.

31. The method of claim 30, wherein the measuring an amount of light scattered by the core stream is effected by a detector.

32. The method of claim 31, wherein the scattered light is continually mapped to a same position on the detector when the change of position of the light source is effected.

33. A telecentricity apparatus comprising:
a light source having various positions;
a detector having a target situated between the light source and the detector; and
an optical arrangement situated between the light source and the detector; and
wherein:
the optical arrangement maintains the same impact position of a light beam from the light source on the detector for the various positions the light source;
a signal from the detector indicates a position to be selected of the various positions of the light source to maximally impinge the target with the light beam.

34. A telecentricity apparatus comprising:
a light source having various positions;
a detector having a target situated between the light source and the detector; and
an optical arrangement situated between the light source and the detector; and
wherein:
the optical arrangement maintains the same impact position of a light beam from the light source on the detector for the various positions the light source;
a position of the various positions of the light source is selected to maximally impinge the target with the light beam;
the telecentricity apparatus further comprises a processor connected to the detector and the light source; and
a signal from the detector via the processor indicates a position to be selected of the various positions of the light source to maximally impinge the target with the light beam.

35. The apparatus of claim 34, wherein the target is a core stream in a flow channel.

36. The apparatus of claim 35, wherein the flow channel is of a cytometer.

37. An illumination apparatus comprising:
a light source;
an optical system, having an axis, at least partially situated between the light source and a target; and
a detector situated on the axis and proximate to the target; and
wherein:
the target moves on axis or off axis;
the light source provides a light beam that is moveable to illuminate the target on axis or off axis;
light from the light beam is mapped to a first position on the detector when the light source is on axis;
light from the light beam is mapped to a second position on the detector when the light source is off axis;
the second position is equivalent to the first position;
the light source is an array of a plurality of lights that are individually selectable to move the light beam;
the illumination apparatus further comprises a processor connected to the detector and the array; and
a signal from the detector via the processor indicates a light to be selected of the array of the plurality of lights to maximally impact the detector with light.

* * * * *